US009235688B2

(12) United States Patent  
Bocirnea

(10) Patent No.: US 9,235,688 B2  
(45) Date of Patent: Jan. 12, 2016

(54) APPARATUS, METHOD AND COMPUTER-READABLE STORAGE MEDIUMS FOR ACKNOWLEDGING RECEIPT OF A HIGHER-PRIORITY MULTIMEDIA OBJECT

(75) Inventor: Radu Catalin Bocirnea, New Westminster (CA)

(73) Assignee: McKesson Financial Holdings, Hamilton (BM)

( * ) Notice: Subject to any disclaimer, the term of this patent is extended or adjusted under 35 U.S.C. 154(b) by 1165 days.

(21) Appl. No.: 13/075,922

(22) Filed: Mar. 30, 2011

(65) Prior Publication Data

US 2012/0254794 A1  Oct. 4, 2012

(51) Int. Cl.  
*G06F 3/0482* (2013.01)  
*G06F 19/00* (2011.01)

(52) U.S. Cl.  
CPC .......... *G06F 19/3456* (2013.01); *G06F 19/327* (2013.01)

(58) Field of Classification Search  
CPC .................................................. G06F 17/3053  
USPC ....................................................... 715/823  
See application file for complete search history.

(56) References Cited

U.S. PATENT DOCUMENTS

| | | | | |
|---|---|---|---|---|
| 8,598,995 B2* | 12/2013 | Schuman et al. | ........ | 340/286.07 |
| 8,627,231 B2* | 1/2014 | Lundy et al. | .................. | 715/823 |
| 2009/0212956 A1* | 8/2009 | Schuman et al. | .......... | 340/573.1 |
| 2009/0315848 A1* | 12/2009 | Ku et al. | ........................ | 345/173 |
| 2010/0057496 A1* | 3/2010 | Fors et al. | ........................ | 705/3 |
| 2014/0085063 A1* | 3/2014 | Schuman et al. | ........ | 340/286.07 |

* cited by examiner

*Primary Examiner* — Namitha Pillai  
(74) *Attorney, Agent, or Firm* — Alston & Bird LLP

(57) ABSTRACT

An apparatus is provided that includes a processor and a memory storing executable instructions that in response to execution by the processor cause the apparatus to direct presentation of a user interface having a list that presents information regarding elements of a plurality of patient exams. The apparatus is also caused to receive an indication of acknowledgment of receipt of a higher-priority one of the exams or information regarding the respective exam. This includes the apparatus being caused to receive an indication of long selection of first information indicating the respective exam's designation as being higher priority, direct presentation of a dialog that includes a user interface element for the acknowledgment, receive an indication of selection of the user interface element, and receive an indication of selection of the first information, without first receiving an indication of user interaction with any other area of the user interface.

18 Claims, 13 Drawing Sheets

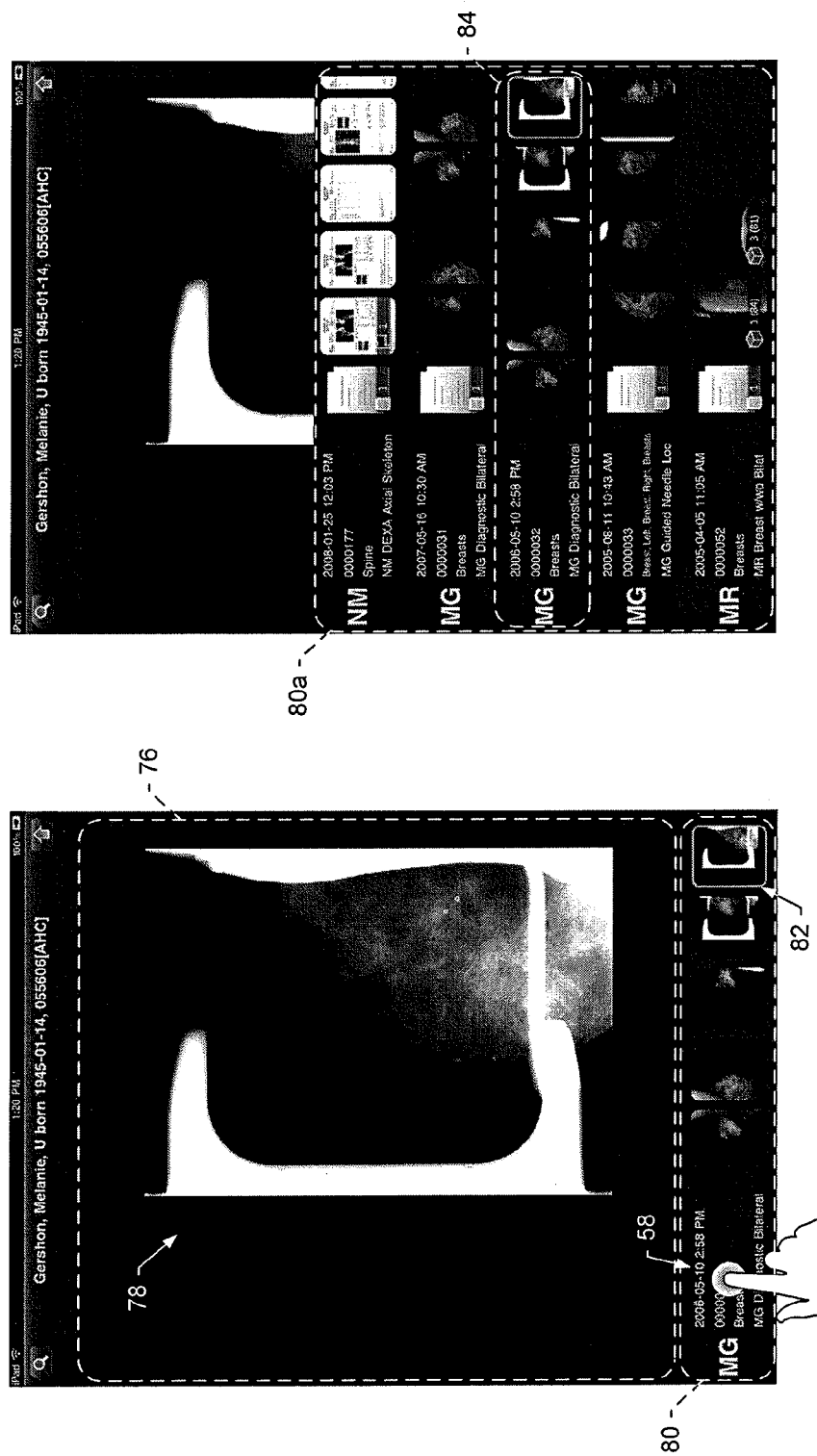

FIG. 8a
FIG. 8b
FIG. 8c

APPARATUS, METHOD AND COMPUTER-READABLE STORAGE MEDIUMS FOR ACKNOWLEDGING RECEIPT OF A HIGHER-PRIORITY MULTIMEDIA OBJECT

FIELD OF THE INVENTION

The present invention generally relates to user interface and methods for interacting with a computer system, and more particularly, to a user interface and method for browsing and selecting a multimedia object, such as a patient exam record, study or the like.

BACKGROUND OF THE INVENTION

Medical imaging often includes creating images and/or video sequences of the human body or parts of the human body for clinical purposes such as examination, diagnosis and/or treatment. These images may be acquired by a number of different imaging modalities including, for example, ultrasound (US), magnetic resonance (MR), positron emission tomography (PET), computed tomography (CT), mammograms (MG) digital radiology (DR), computed radiology (CR) or the like. In a number of example medical imaging workflows, such as in the case of a picture archiving and communication system (PACS), an image study for a patient may include one or more acquired images of the patient along with information that may reside with or otherwise accompany the images. This information may include, for example, a study identifier (ID) as well as patient information such as the patient's name, demographics, medical record number or the like.

Once a patient study has been created, the study may be stored in a database of a central storage device for later retrieval by a workstation where the study may be reviewed by a medical professional such as a radiologist who may make one or more diagnoses or other assessments of the patient from the study, and record those diagnoses or other assessments in a text-based report. This report may then be stored in an information system such as a hospital information system (HIS), radiology information system (RIS) or the like, where the report may be linked or otherwise associated with the image study such as by study ID, patient name, medical record number or the like.

SUMMARY OF THE INVENTION

In light of the foregoing background, exemplary embodiments of the present invention provide an apparatus, method and computer-readable storage medium for browsing and selecting a multimedia object, such as a patient exam that may include an image study and associated report. According to one aspect of exemplary embodiments of the present invention, an apparatus is provided that includes a processor and a memory storing executable instructions that in response to execution by the processor cause the apparatus to at least perform a number of functions. The apparatus is caused to direct presentation of a user interface having a list that presents information regarding one or more elements of each of a plurality of patient exams, where one or more of the plurality of patient exams is designated as being of higher priority than others of the plurality of patient exams. For each higher-priority patient exam, the information presented by the list of patient exams includes selectable information indicating the patient exam's designation as being higher priority.

The apparatus is also caused to receive an indication of user acknowledgment of receipt of a higher-priority patient exam or information regarding the higher-priority patient exam. This includes, in order, the apparatus being caused to receive an indication of user long selection of the information indicating the respective patient exam's designation as being higher priority, and direct presentation of a dialog that includes a selectable user interface element for the acknowledgment. The user acknowledgment also includes the apparatus being caused to receive an indication of user selection of the selectable user interface element. And the user acknowledgment includes the apparatus being caused to receive an indication of user selection of the information indicating the respective patient exam's designation as being higher priority, without first receiving an indication of user interaction with any other area of the user interface.

The apparatus may be further caused to direct adjustment of the user interface in response to receipt of the indication of user acknowledgment of receipt of a higher-priority patient exam or information regarding the higher-priority patient exam. This may include the apparatus being caused to direct removal from the list of patient exams of the information indicating the respective patient exam's designation as being higher priority.

In a number of examples, the apparatus may be caused to receive an indication of user acknowledgment of receipt of a first higher-priority patient exam or information regarding the first higher-priority patient exam. In these examples, the apparatus may be further caused to receive an indication of user deferral of acknowledgment of receipt of a second higher-priority patient exam or information regarding the second higher-priority patient exam.

In a first of the examples, the deferral may include the apparatus being caused to receive an indication of user long selection of the information indicating the respective second patient exam's designation as being higher priority, and direct presentation of the dialog that includes a first selectable user interface element for the acknowledgment, and a second selectable user interface element for the deferral of the acknowledgment. The deferral may also include the apparatus being caused to receive an indication of user selection of the second selectable user interface element, and receive an indication of user selection of the information indicating the respective patient exam's designation as being higher priority, without first receiving an indication of user interaction with any other area of the user interface.

In a second of the aforementioned examples, the deferral may include the apparatus being caused to receive an indication of user long selection of the information indicating the respective second patient exam's designation as being higher priority, and direct presentation of the dialog that includes a first selectable user interface element for the acknowledgment, and a second selectable user interface element for the deferral of the acknowledgment. The deferral of this other example may also include the apparatus being caused to receive an indication of user selection of either the first selectable user interface element or second selectable user interface element, and receive an indication of user interaction with any area of the user interface other than the information indicating the respective patient exam's designation as being higher priority, without first receiving an indication of user selection of the information indicating the respective patient exam's designation as being higher priority.

In a third of the aforementioned examples, the deferral may include the apparatus being caused to receive an indication of user long selection of the information indicating the respective patient exam's designation as being higher priority, and direct presentation of a dialog that includes a selectable user interface element for the acknowledgment. The deferral in this third example may also include the apparatus being caused to receive an indication of user selection of the selectable user interface element, and receive an indication of user interaction with any area of the user interface other than the information indicating the respective patient exam's designation as being higher priority, without first receiving an indication of user selection of the information indicating the respective patient exam's designation as being higher priority.

BRIEF DESCRIPTION OF THE DRAWINGS

Figure 1:
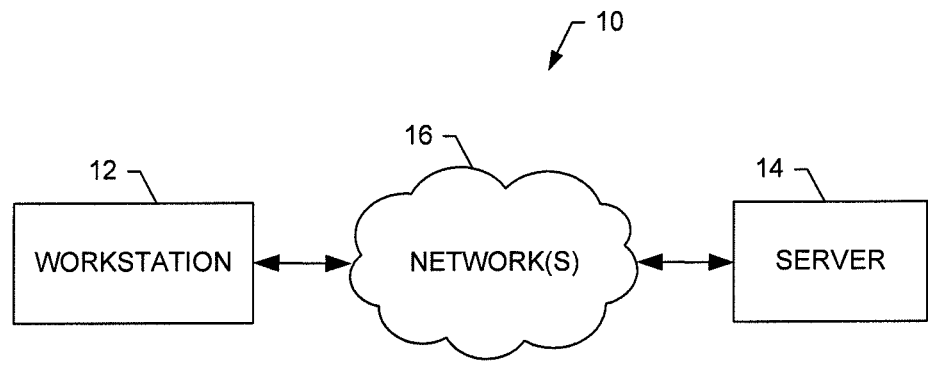
Figure 2:
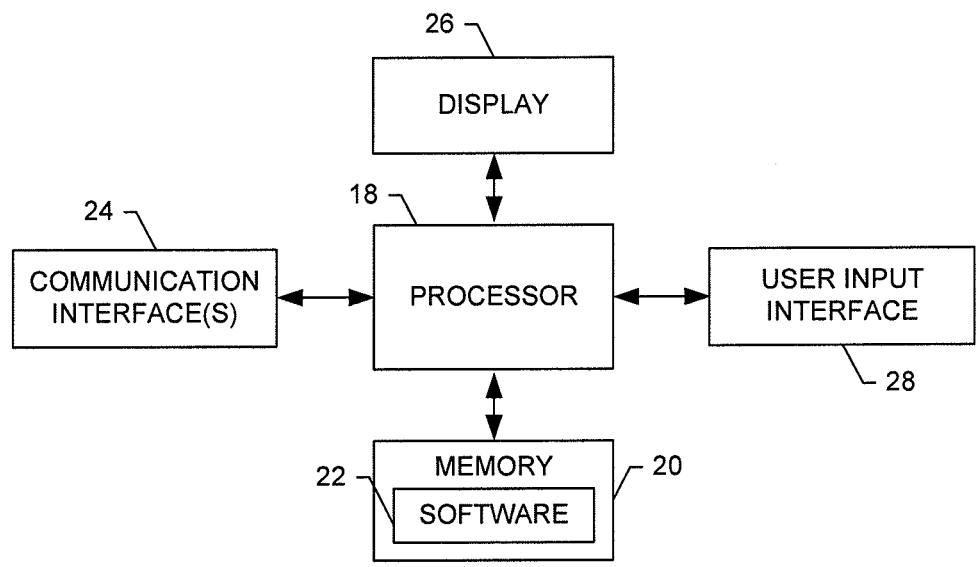
Figure 3:
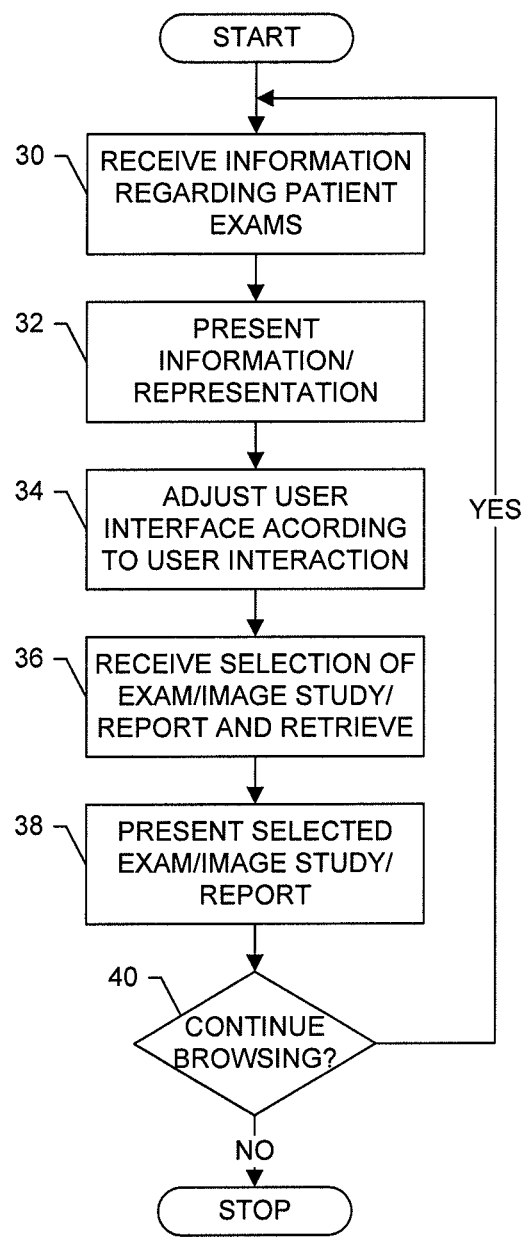

Having thus described the invention in general terms, reference will now be made to the accompanying drawings, which are not necessarily drawn to scale, and wherein:

FIG. 1 is a schematic block diagram of a system configured to operate in accordance with exemplary embodiments of the present invention;

FIG. 2 is a schematic block diagram of an apparatus configured to operate as a workstation or server, in accordance with exemplary embodiments of the present invention;

FIG. 3 is a flowchart illustrating various steps in a method according to exemplary embodiments of the present invention; and FIGS. 4-12 illustrate example user interface displays according to exemplary embodiments of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. For example, references may be made herein to directions and orientations including up, down, right and left; it should be understood, however, that any direction and orientation references are simply examples and that any particular direction or orientation may depend on the particular object, and/or the orientation of the particular object, with which the direction or orientation reference is made. Like numbers refer to like elements throughout.

FIG. 1 illustrates a system 10 that may benefit from exemplary embodiments of the present invention ("example," "exemplary" and like terms as used herein refer to "serving as an example, instance or illustration"). As shown, the system includes one or more workstations 12, and may further include one or more servers 14. Generally, the workstation and server of exemplary embodiments of the present invention may comprise, include or be embodied in one or more portable or fixed electronic devices, such as one or more of a portable media player, smartphone, portable digital assistant (PDA), tablet computer, laptop computer, desktop computer, server computer or the like.

In one example embodiment, the workstation 12 may form part of one or more of a hospital information system (HIS), radiology information system (RIS), picture archiving and communication system (PACS) or the like. The workstation may therefore include a HIS workstation, RIS workstation, PACS workstation or the like. In other example embodiments, the workstation may include a workstation configured to support multiple ones of a HIS, RIS and/or PACS workstation, logically separated but co-located within the respective workstation.

Similar to the workstation 12, the server 14 may be a server of one or more of a HIS, RIS, PACS or the like. The server may therefore include a HIS server, RIS server, PACS server or the like, each of which may be configured to interface with a respective database. In other example embodiments, the server may include a server configured to support multiple ones of a HIS, RIS and/or PACS server, logically separated but co-located within the respective server.

The workstation 12 and server 14 may be configured to directly and/or indirectly communicate with one another in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G, 3G or 4G communication techniques, local area network (LAN), wireless LAN (WLAN) techniques or the like. In accordance with various ones of these techniques, the workstation(s) and server may be coupled to and configured to communicate across one or more networks 16. The network(s) may include any of a number of different combinations of one or more different types of networks, including data and/or voice networks. For example, the network(s) may include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the workstation and server.

Reference is now made to FIG. 2, which illustrates a block diagram of an apparatus that may be configured to operate as or otherwise perform one or more functions of a workstation 12 and/or server 14. Although shown in FIG. 1 as separate apparatuses, in some embodiments, the apparatus may support both a workstation and server, logically separated but co-located within the apparatus. The apparatus of exemplary embodiments of the present invention includes various means for performing one or more functions in accordance with exemplary embodiments of the present invention, including those more particularly shown and described herein. It should be understood, however, that either or both of the apparatuses may include alternative means for performing one or more like functions, without departing from the spirit and scope of the present invention.

As shown in FIG. 2, the apparatus may include a processor 18 connected to a memory 20. The memory may include volatile and/or non-volatile memory, and typically stores content, data or the like. In this regard, the memory may store one or more software applications 22, modules, instructions or the like for the processor to perform steps associated with operation of the apparatus in accordance with embodiments of the present invention. The memory may also store content transmitted from, and/or received by, the apparatus. As described herein, the software application(s) may each comprise software operated by the apparatus. It should be understood, however, that any one or more of the software applications described herein may alternatively be implemented by firmware, hardware or any combination of software, firmware and/or hardware, without departing from the spirit and scope of the present invention.

In addition to the memory 20, the processor 18 may also be connected to at least one interface or other means for displaying, transmitting and/or receiving data, content or the like, such as in accordance with USB, RF, BT, IrDA, WLAN, LAN, MAN, WAN (e.g., Internet), PSTN techniques or the like. In this regard, the interface(s) may include at least one communication interface 24 or other means for transmitting and/or receiving data, content or the like. In addition to the communication interface(s), the interface(s) may also include at least one user interface that may include one or more earphones and/or speakers, a display 26, and/or a user input interface 28. The user input interface, in turn, may include any of a number of devices allowing the apparatus to receive data from a user, such as a microphone, a keypad, a touch-sensitive surface (integral or separate from the display), a joystick, or other input device.

Reference is now made to FIG. 3, which illustrates various operations in a method of browsing and selecting a multimedia object, and in which the operations may be performed by or at a workstation 12. In this regard, the workstation 12 may be configured to interface with a database of multimedia objects, which may be local to (e.g., in memory of) the workstation or remote from the workstation such as local to or otherwise in communication with the server 14. As shown in the figures and described herein, the multimedia objects may include patient exams with medical image studies and their associated reports, such as from a PACS, HIS, RIS or the like. It should be understood, however, that the multimedia objects may include any of a number of different multimedia objects (e.g., text, audio, video or combinations of text, audio or video) related or directed to any of a number of different topics or subjects.

The method of one example embodiment may include receiving information regarding a number of patient exams, as shown in block 30. A patient exam may include an image study with one or more images and/or one or more video sequences (generally "images"), and may include one or more associated reports. Additionally, a patient exam may include other information including, for example, documents associated with the study such as scanned or electronic documents, forms, diagrams or the like. It should be understood, however, that a patient exam may not include a report such as in an instance in which the respective image study is unreported. Thus, the number of patient exams may include one or more patient exams each of which includes both an image study and associated report, and may include one or more patient exams each of which includes an image study but does not include (or does not yet include) an associated report.

As or after the information regarding patient exams is received, the method may include generating and presenting or directing presentation of a user interface including the information or a representation of the information, as shown in block 32. A user may interact with the user interface to browse the information; and as or after each user interaction, the method may include receiving an indication of the user interaction, and adjusting or directing adjustment of the user interface in accordance with the user interaction, as shown in block 34. This may facilitate the user locating a patient exam of interest, or for a patient exam, an image study or report of interest. The user may then interact with the user interface to select a patient exam, or select an image study or report of a patient exam.

As or after the user interaction to select a patient exam, or select an image study or report of a patient exam, the method may include receiving an indication of the user interaction, and retrieving or directing retrieval of the selected patient exam, image study or report, as shown in block 36. The method may then include presenting or directing presentation of the selected patient exam, image study or report by the user interface, as shown in block 38. In various instances, as the user interface presents the selected patient exam, image study or report, the user interface may continue to present information regarding one or more patient exams or a representation of the respective information. Alternatively, the user may interact with the user interface to recall the information or representation of information regarding one or more patient exams. In these instances, the method may return to presentation of the respective information or representation for browsing and selection of a patient exam, image study or report, as shown in block 40. For more information regarding manners by which information including that for a number of patient exams or a selected patient exam may be received, retrieved, processed or otherwise presented, see U.S. patent application No. 13/075,495, entitled: Method, Apparatus and Computer Program Product for Normalizing and Processing Medical Images; U.S. patent application No. 13/075,547, entitled: Method, Apparatus and Computer Program Product for Displaying Normalized Medical Images; and U.S. patent application No. 13/075,593, entitled: Methods, Apparatuses and Computer Program Products for Providing Adaptive Rendering Quality Degradation, all of which are filed concurrently herewith. The contents of all of the foregoing patent applications are hereby incorporated by reference in their respective entireties.

Reference is now made to FIGS. 4-12, which illustrate example user interface displays according to example embodiments of the present invention. As shown and described herein, the user interface and interactions with the user interface may be by a workstation 12 including a touch-sensitive surface integral with its display. In these instances, touch gesture interactions described with reference to the user interface may be more particularly accomplished by interactions with the touch-sensitive surface/display presenting the user interface. It should be understood, however, that the same or similar user interface displays and interactions may be carried out by workstations including other types of user input interfaces. Also, although the interactions may be described with reference to a user interacting with the touch-sensitive surface with one or more of their fingers, the user may instead interact with the touch-sensitive surface with any of a number of other appropriate objects such as a stylus.

Figure 4:
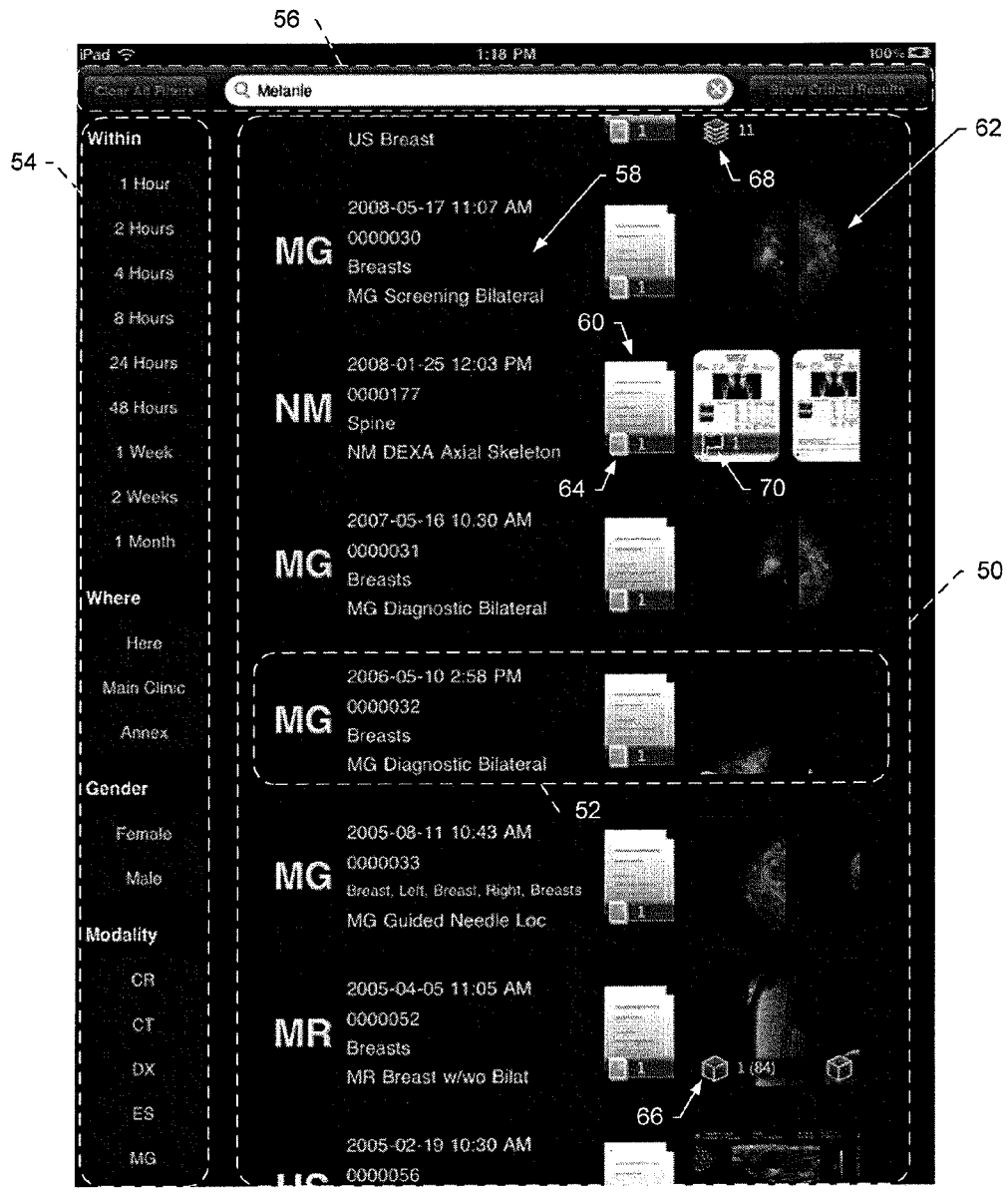

The user interface of one example embodiment may be configured to present a number of different views allowing a user to browse and view patient exams, and in which each view may include one or more windows, regions or the like (generally "regions"). FIG. 4 illustrates a first view of the user interface including a number of regions. In a first region 50, the user interface may include a first list of patient exams 52 that identifies a plurality of patient exams by presenting various pieces of information regarding the respective exams. In a second region 54 and in a third region 56, the user interface may include various means by which a user may filter the first list of patient exams. In the second region, for example, the user may filter the first list of patient exams according to one or more parameters of the patients or their exams. And in the third region, for example, the user may filter the first list of patient exams by keyword or, as explained further below, by exams designated as being of higher priority than other exams. As described herein, filtering the first list by keyword may include application of any of a number of different search engine algorithms, which may return patient exams that match the keyword filter, and may also rank the patient exams so that those deemed most relevant to the filter are listed first.

Turning more particularly now to the first region 50, the first list of patient exams 52 may include any of a number of different pieces of information for each exam. This information may include textual information 58 such as a time/date, study ID, part of the body to which the exam is directed, modality and type of images acquired. The information may also include thumbnail images representing one or more elements of the patient exam. In one example, a thumbnail image may represent one or more reports 60, or one or more images or sequences of images of an image study 62. These thumbnail images may be general representative images, or in one example embodiment, one or more of the thumbnail images may be of the actual elements. The user interface may overlay one or more of the thumbnail images with information regarding the element of the exam study to which it pertains. For a thumbnail of a report, this further information may include, for example, a graphical information such as a static or animated icon 64 or other image (generally referred to as an "icon") representing a report and text depicting the number of reports in the exam.

For an image study, the user interface may overlay the thumbnail image 62 with information such as that representing or otherwise depicting the type and/or number of image(s) or video sequence(s) of the study. More particularly for example, for a volumetric sequence of images, the information may include an icon 66 representing a three-dimensional (3D) volume and text depicting the number of volumes in the sequence and (parenthetically) the number of images in the sequence. For other multi-image sequences, the information may include, for example, an icon 68 representing a stack of images and text depicting the number of images in the stack. For a video sequence, the information may include, for example, an icon representing a video sequence and text depicting the length of the video sequence. Even further, in various instances in which a thumbnail image represents an image or sequence of images including one or more images designated as key images, the information may include an icon 70 representing key images and text depicting the number of key images.

Figures 5A, 5B:
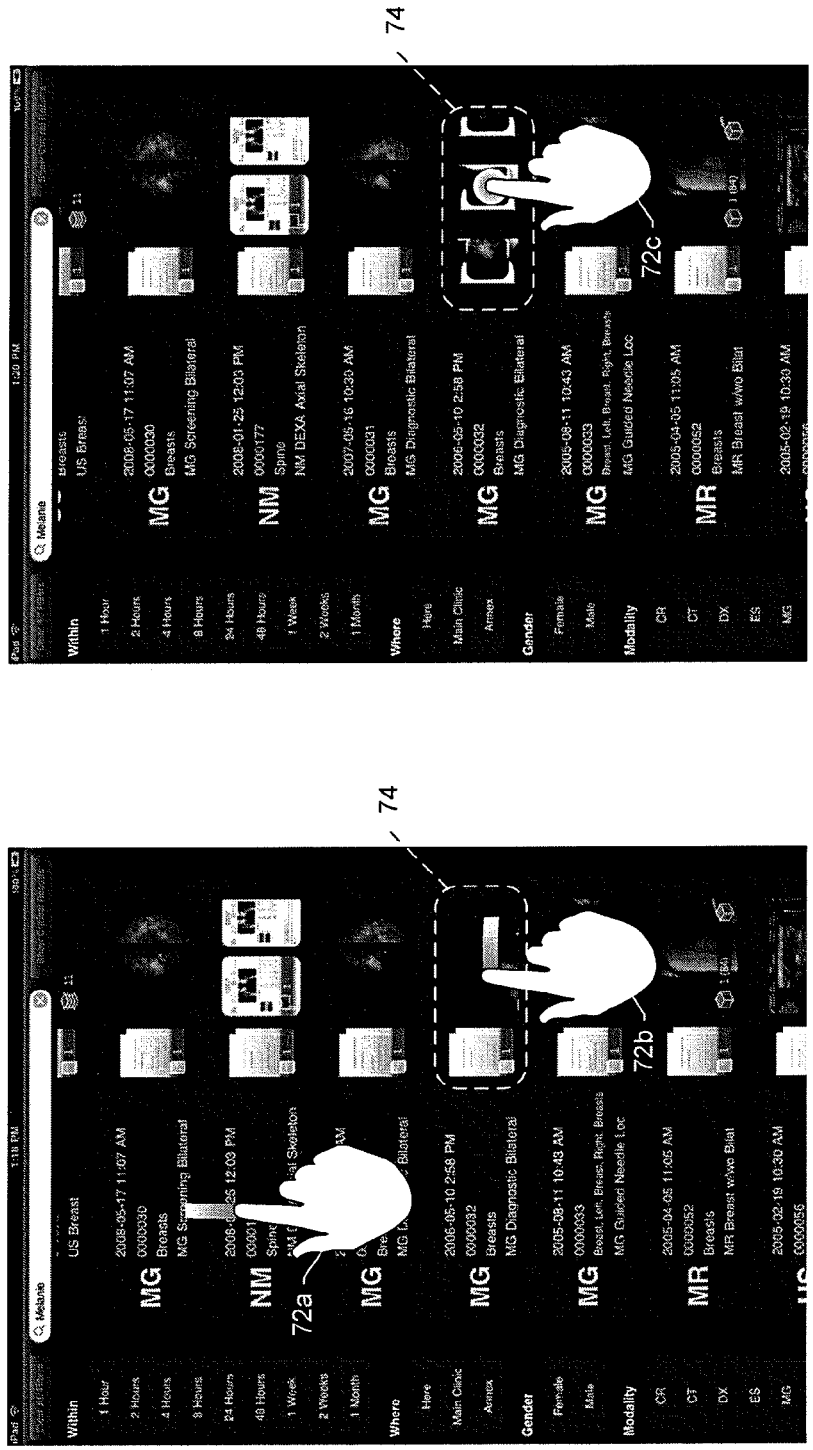

The first list of patient exams 52 may fill all or a portion of the first region 50, and may even extend outside the first region viewable by the user. In instances in which the first list extends outside the first region, the first list may be scrollable such that the user may scroll through the patient exams to view information for those that may not otherwise be viewable. As shown in FIG. 5*a*, for example, this may be accomplished by the user dragging (shown) or flicking their finger 72*a* up or down in contact with the first region. Similarly, for one or more of the listed patient exams, the thumbnail images representing elements of the patient exam may extend outside the boundaries of the first region. In these instances, the area 74 of the first region including thumbnails of the study may be scrollable such that the user may scroll through the thumbnail images to view those that may not otherwise be viewable. As also shown in FIG. 5*a* and into FIG. 5*b*, this may be accomplished, for example, by the user dragging or flicking their finger 72*b* left or right in contact with the area including thumbnails of the study.

As also shown in FIG. 5*b*, to view an exam from the first list of exams 52, the user may select the exam such as by tapping their finger 72*c* on the thumbnail representation of an element of the respective exam. As shown in FIG. 6*a*, the user interface may respond to selection of an exam by presenting a second view including a number of regions, a first region 76 of which may display the selected element of the respective exam. In FIG. 6*a*, for example, the user's selection of the thumbnail of FIG. 5*b* may result in the user interface presenting the element 78 represented by the respective thumbnail.

In this second view, the user interface may also include a condensed second region 80 for presenting a second list of patient exams that, similar to the first list, identifies a plurality of patient exams by presenting various pieces of information regarding the respective exams. This second region may be smaller in size than the first region 50 of the first view, such as by being sized so that fewer patient exams may be viewable at any given instance. As shown in FIG. 6*a*, for example, the second region of the second view may be sized such that information for only one patient exam may be completely viewable at a time. This patient exam may be the selected patient exam, and the selected element presented in the first region 76 of the second view may be set apart in the second region such as by presenting a border 82 around the thumbnail representing the respective element.

The second list of patient exams in the second region 80 of the second view may include information for the same patient exams in the first list of patient exams 52 in the first region 50 of the first view. In one example embodiment, however, the second list of patient exams includes information for patient exams for the same patient as that of the selected patient exam. Thus, in various instances, the second list of patient exams may include information for one or more exams different from the patient exams of the list in the first region of the first view.

The second list of patient exams in the second region 80 of the second view may be scrollable similar to the first list of patient exams 52 in the first region 50 of the first view; and likewise, the elements of the second list of patient exams may be similarly scrollable as the elements of the first list of patient exams. Similar to the first view, to view an exam from the second list of exams, the user may select an exam such as by tapping their finger on a thumbnail representation of an element of the exam. The user interface may respond to this selection by presenting the respective element in the first region 78 and setting apart the respective thumbnail in the second region of the second view, such as by moving the border 82 from the thumbnail of the previously-presented element to the thumbnail of the currently-presented element.

In one example embodiment, the user interface may expand the size of the condensed second region 80 of the second view—and hence the second list of patient exams in the second region—in response to user input. As shown in FIG. 6*a* into FIG. 6*b*, for example, this user input may include the user tapping their finger 72*d* on the textual information 58 for an exam viewable in the condensed second region. As shown in FIG. 6*b*, the expanded second region 80*a* may, in one example, include the scrollable second list of patient exams of the particular patient whose patient exam the user selected from the first list of patient exams 52. In one example, the second list of exams in the expanded second region may be presented in chronological or reverse-chronological order, with the currently-selected exam 84 placed in the middle of the initially-viewable patient exams so that the user may more readily identify newer and older patient exams of the respective patient.

Figure 7B:
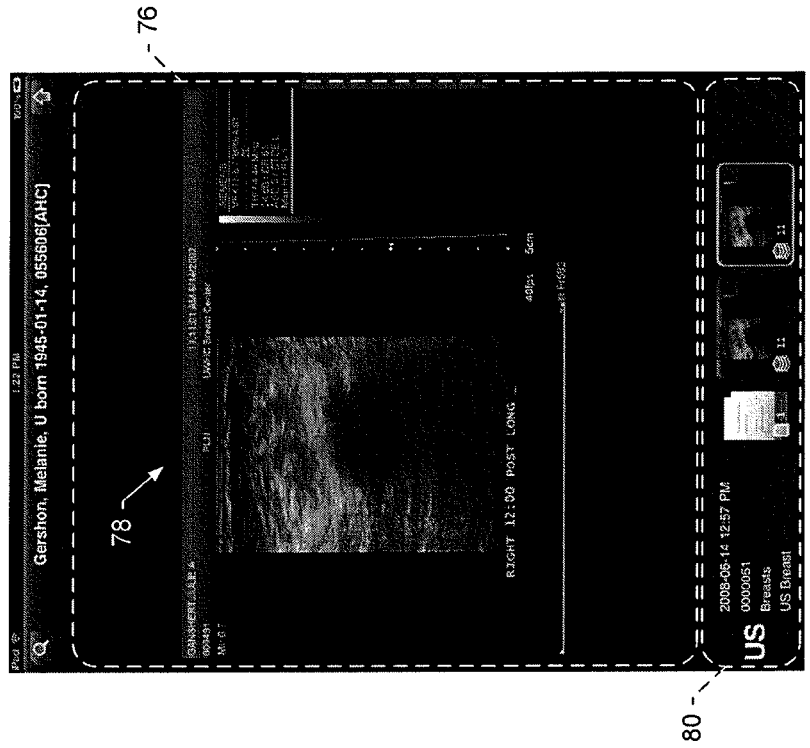
Figure 7A:
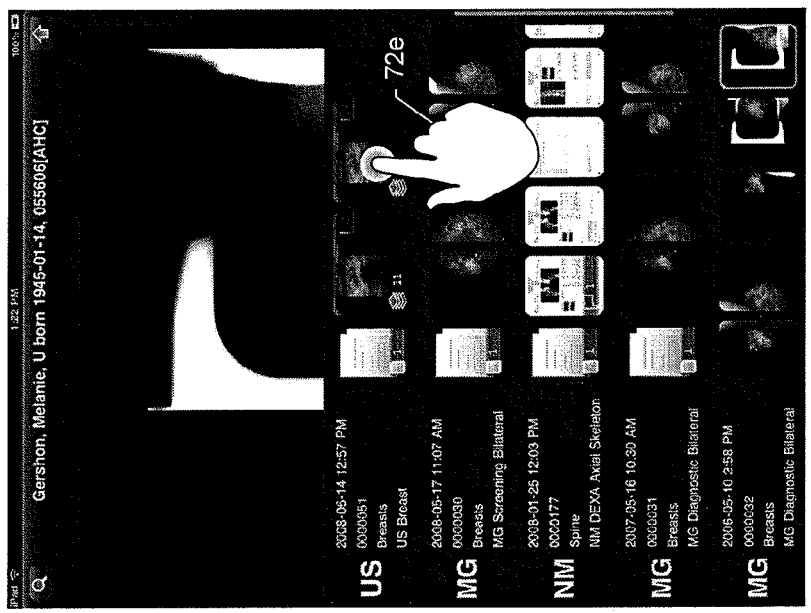
Figure 10:
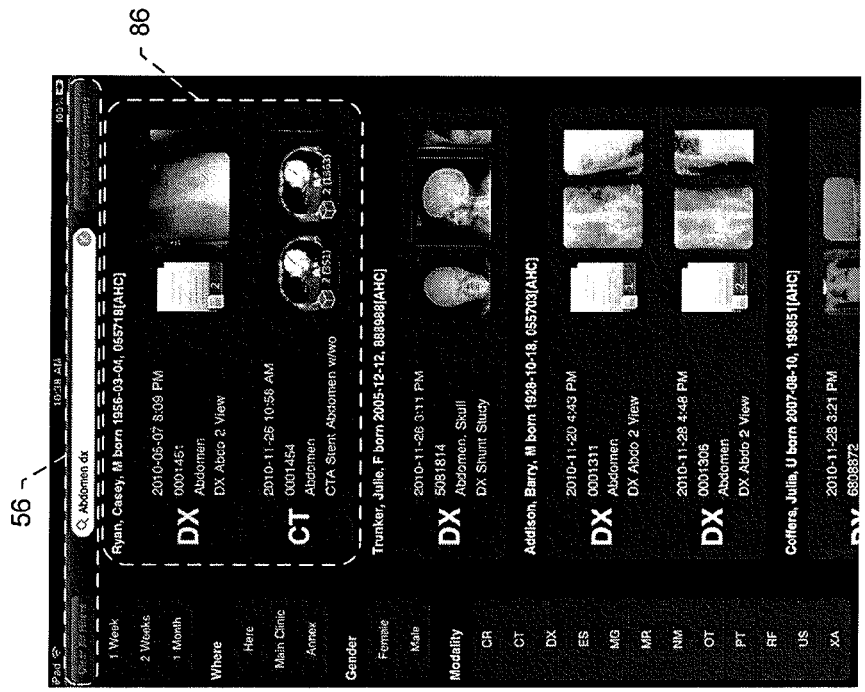
Figure 9:
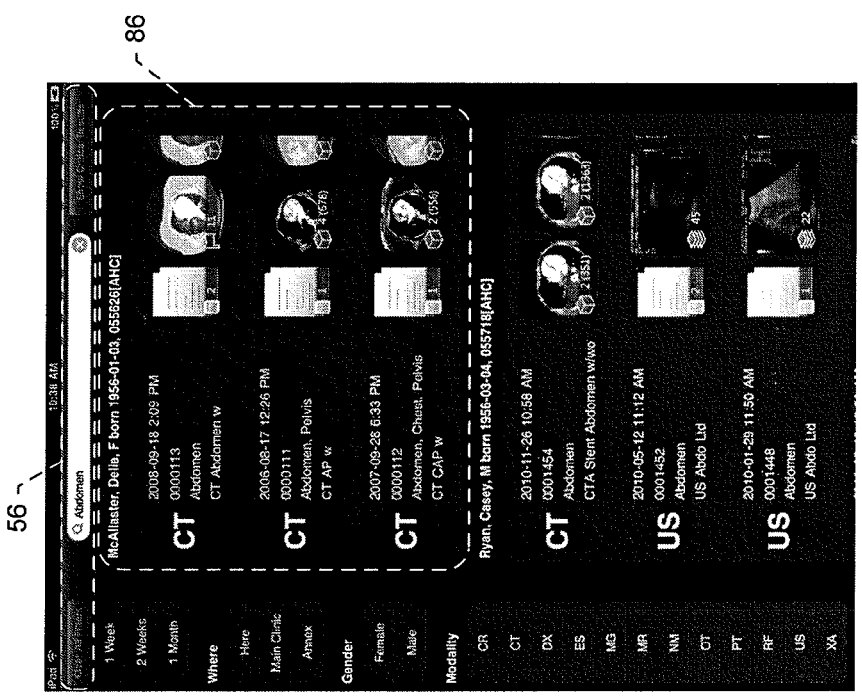

A patient exam may be selected from the second list of patient exams in the expanded second region 80*a* in a manner similar to selecting a patient exam from the first list of patient exams 52 presented in the first view. That is, the user may select an exam such as by tapping their finger 72*e* on the thumbnail representation of an element of the respective exam, as shown in FIG. 7*a*. As shown in FIG. 7*b*, the user interface may respond to selection of an exam by displaying the selected element 78 of the exam in the first region 76 of the second view. Additionally, the user interface may collapse the expanded second region back to the second region 80 for displaying information for at least the currently-selected exam.

As indicated above, the second list of patient exams in the condensed second region 80 of the second view may be scrollable similar to the first list of patient exams 52 in the first region 50 of the first view. That is, as shown in FIG. 8a, the second list of patient exams may be scrollable by a user dragging or flicking (shown) their finger 72f up or down in contact with the second region. In one example embodiment, as the user scrolls through the second list of patient exams, the element 78 presented in the first region 76 of the second view may change according to the patient exam information viewable in the second region, as shown from FIG. 8a into FIGS. 8b and 8c for reports of patient exams viewable in the second list.

In instances in which the user scrolls through the second list in the condensed second region 80, the element 78 presented in the first region 76 of the second view may be selected in a number of different manners. In one example, the presented element may be an element pre-selected or otherwise designated as the most-relevant element of the exam information of which is viewable in the condensed second region. In various instances, the presented element may be further determined to be logically related to the element it replaces in the first region. For example, an image or group of images may be logically related to the image or group of images previously displayed in the first region (e.g., a sequence of images of the same type). In another example, as shown in FIGS. 8a-8c, a report may be logically related to other reports.

Returning to the first view of the user interface shown in FIG. 4, the patient exams of the first list of patient exams 52 in the first region 50 may be ordered in a number of different manners. As explained above, the first list of patient exams may be filtered by keyword, and in such instances, the first list may include information for patient exams that match the keyword filter and may be presented in a ranked order so that exams deemed most relevant to the filter are listed first. In accordance with one example embodiment, the patient exams of the first list may be clustered by patient, and for each patient in an instance in which a keyword filter is applied, the information for exams may be presented in a ranked order according to an applied keyword filter. This is shown for example in FIGS. 9 and 10 in which the information for patient exams is clustered by patient 86 and, for each patient, ordered by application of a keyword filter entered into a text-entry field in the third region 56. From the user's perspective, the filtered patient exams may appear to be re-ranked as a result of patient clustering.

Let $S=\{O_1, O_2, \ldots O_k, \ldots O_n; R_k \geq R_{k+1}\}$ represent a set of ordered patient exams returned as the results of an applied search engine algorithm (a subset of the first list of patient exams). In the preceding, $O_k$ represents an exam of a single patient, and as determined by the search engine algorithm, $R_k$ represents the rank of exam $O_k$. Given two patient exams $O_k$ and $O_j$, $O_k$ is more relevant than $O_j$ if and only if $R_k > R_j$. In accordance with example embodiments of the present invention, the set of ordered patient exams S may be transformed to a set of clustered and ordered patient exams $S_c=\{C_1, C_2, \ldots C_x, \ldots C_m; RC_k \geq RC_{k+1}\}$. In the transformed set, $C_x$ represents the ordered set of patient exams $\{O_p \ldots O_q \ldots O_r\}$ belonging to patient $P_x$ in the set of patients $P=\{P_1 \ldots P_m\}$, and $R_q \geq R_{q+1}$. Also in the transformed set, $RC_k$ represents the ranking of $C_k$, which in various example embodiments may be set as the rank of the first ordered exam in $C_k$ (the highest rank of any element in $C_k$) or as a weighted average of the ranks of the exams in $C_k$.

In various instances, the user interface may be configured to limit the number of patient exams in the first list of patient exams 52, or rather the filtered first list of patient exams. For example, the number of patient exams may be limited to a particular number of exams per patient. In this example, the user interface may include means for expanding the exams for a patient such as to present additional exams, or an entire list of exams including more than the particular number of exams.

As indicated above, in the third region 56 of the first view, the user may filter the first list of patient exams by exams 52 designated as being of higher priority than other exams. The first list of patient exams may therefore include one or more exams designated as being higher priority than other exams, and within the higher-priority exams, the exams may be further ranked by priority or importance. In one example, the higher-priority exams may include exams that have important information associated with them in the form of a "critical result" (a "critical result" is a form of communicating an unexpected and potentially grave result of a radiological exam).

As also indicated above, in instances in which the first list of patient exams extends outside the first region 50 shown to the user, the first list may be scrollable such that the user may scroll through the patient exams 52 to view information for those that may not otherwise be viewable. In accordance with one example embodiment, the user interface may be configured to provide an alert in an instance in which the first list of patient exams includes an exam of higher priority than any exam viewable in the first region. The higher-priority patient exam not viewable in the first region may be, for example, a patient exam scrolled out of the first region or a patient exam filtered out of the first list of patient exams. Although described herein with reference to the first list of patient exams, it should be understood that the user interface may be equally configured to provide an alert in an instance in which the second list of patient exams includes an exam of higher priority than any exam viewable in the condensed second region 80 or extended second region 80a.

Figure 11B:
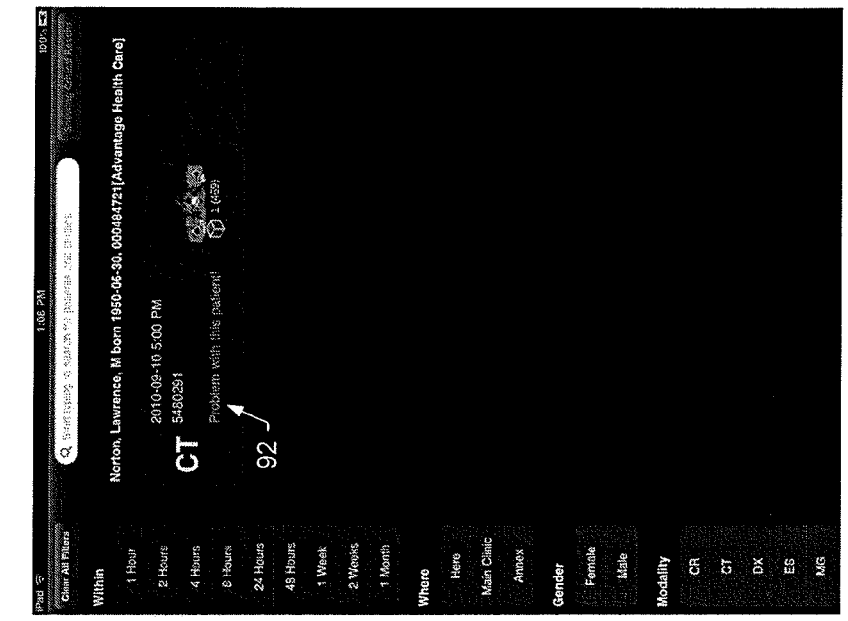
Figure 11A:
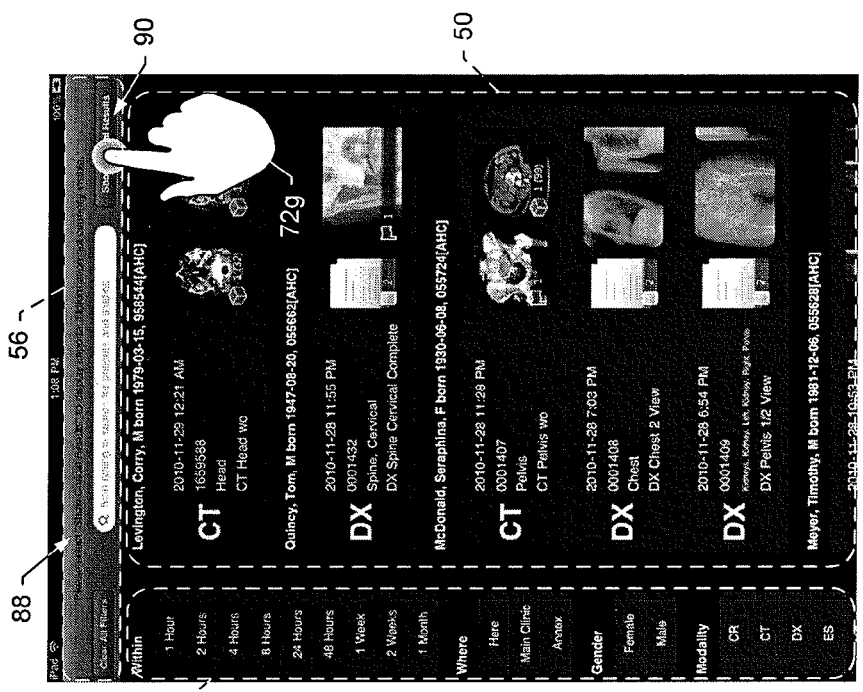

The alert may include any of a number of different types of alerts, such as a visual, audible and/or tactile (e.g., vibration) alert. As shown in FIG. 11a, in one example embodiment, the alert may include a visual alert in the form of a banner 88 that may be presented in the first view, such as along with or above the third region 56 of the first view. The banner may be set apart from other elements of the user interface such as by being larger in size or different in color. In the example of FIG. 11a, the banner (and possibly the third region in instances in which the banner is displayed) may have a background color (e.g., orange) different from the background colors of other portions of the first view such as the first and second regions 50, 54 (e.g., black, blue). The banner may further include textual information that may notify a user of the availability of higher-priority patient exams, and may direct the user as to how to view information for the respective exams.

In one example embodiment, as shown in FIG. 11a, one of the regions 50, 54, 56 or the banner 58 or other visual alert may include a selectable button 90 or other selectable user interface element to direct the user interface to filter the first list of patient exams to present information for the higher-priority exams. The user may then tap their finger 72g on the button to direct the user interface to filter the first list to only list the higher-priority exams in the first region. This is shown, for example, in FIG. 11a leading into FIG. 11b. The information for the higher-priority exam may include the same type of information as for the other exams of the first list of patient exams, but may additionally or alternatively include one or more pieces of information 92 indicating its designation as a higher-priority exam. This information may include an icon representing its designation as higher priority and/or text depicting the designation and/or an explanation of the designation or the reason for the exam's designation. And the information may be set apart from other information such as by being larger in size or different in color. As shown in FIG. 11b, for example, the information for the higher-priority exam may indicate a "critical result" by indicating that for a patient exam, there may be a "Problem with this patient!."

Figures 11C, 12A:
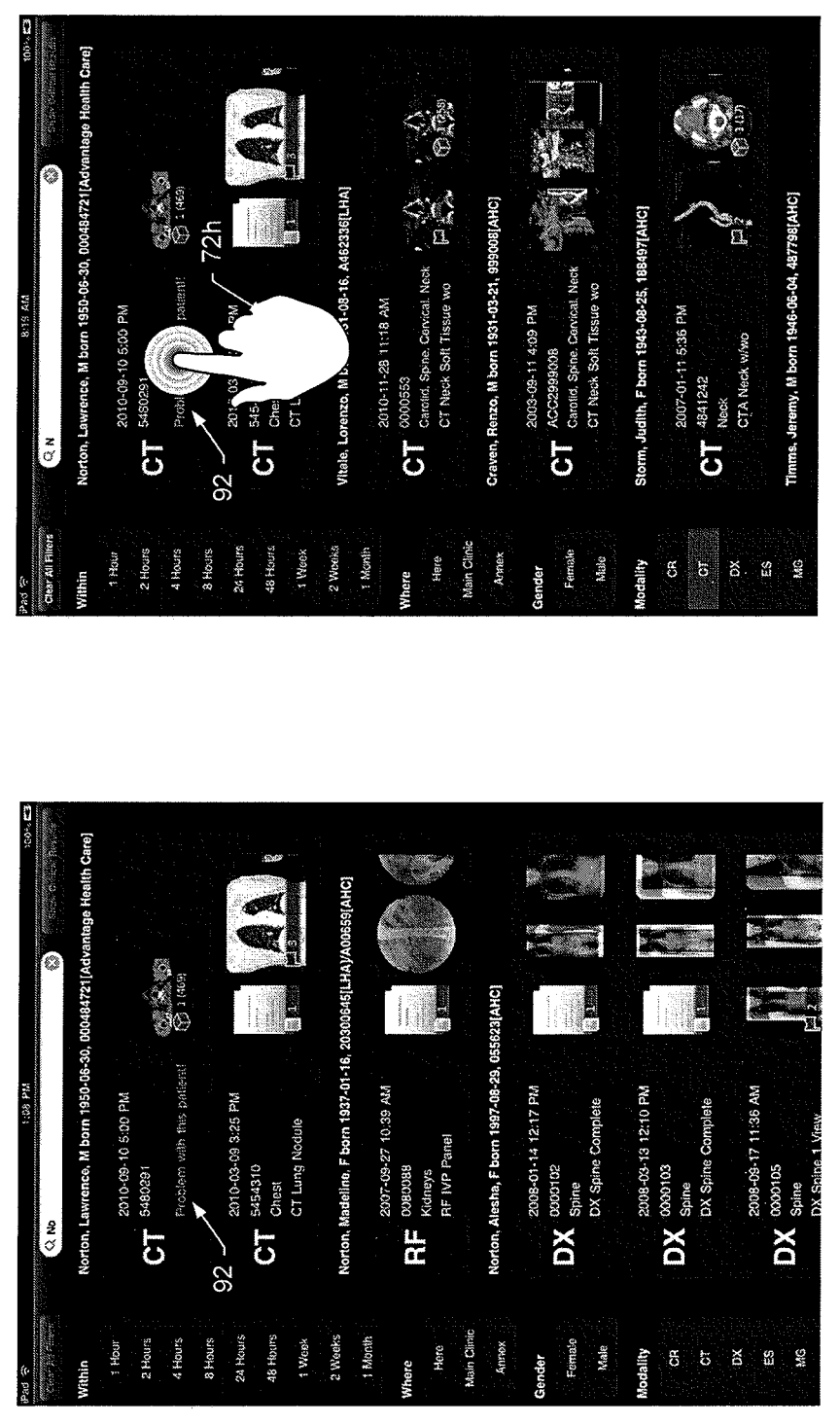

The user interface may be configured to cease presentation of the alert in response to information for a higher-priority exam of the first list of patient exams 52 becoming visible in the first region 50. In this regard, information for the higher-priority exam may become visible in the first region of the first view in a number of different manners. As shown in FIG. 11b, for example, information for the higher-priority exam may become visible in response to filtering the first list by those designated as being higher-priority exams. In another example, as shown in FIG. 11c, information for the higher-priority exam may become visible as the user scrolls through the first list of patient exams in the first region. In either instance, in the event information for the higher-priority exam ceases to be visible in the first region, the user interface may be configured to once again present the alert, such as in a manner similar to that described above.

The alert may be continuously presented until information for a higher-priority exam of the first list of patient exams 52 becomes visible in the first region 50. In other examples, the alert may be presented for a shorter period of time, or may be presented at regular or irregular intervals, until the aforementioned condition is satisfied.

Consider an example in which the list includes information for multiple higher-priority exams none of which is further ranked as being of higher priority than the others. In this example, the user interface may be configured to present the alert in instances in which no information for any of the higher-priority exams is viewable in the first region 50, but cease presentation of the alert when information for at least one of the higher-priority exams becomes viewable in the first region. The alert may not be presented as long as information for one of the higher-priority exams is viewable, even if information for others of the higher-priority exams is not viewable.

Consider another example in which the list includes information for multiple higher-priority exams none of which is further ranked has being of higher priority than the others. In this other example, the user interface may be configured to present the alert only in instances in which both of the following conditions are satisfied: the list is not filtered to show only higher-priority exams, and information for at least one higher-priority exam is not viewable in the first region 50. In this other example, in instances in which the list is filtered to show only higher-priority exams, the alert may not be displayed even if the set of exams does not fit within the first region—e.g., the user would have to scroll to view information for the exams not otherwise viewable. Also of note in this other example, exams not viewable in the first region may include exams that are not viewable as a result of keyword filtering. Thus, the higher-priority exam does not need to be part of the exams that can be accessed as a result of scrolling through the list.

The designation of a patient exam as being higher-priority may facilitate the user noticing the exam in the first list of patient exams 52, such as by the list including information indicating the exam's designation as a higher-priority exam. This, in turn, may facilitate the user acknowledging receipt of the higher-priority exam or information regarding the higher-priority exam. In one example embodiment, the user interface may be configured to relieve an exam from its higher-priority designation—and hence its information indicating the exam's designation—in response to the user acknowledging receipt of the respective exam or information regarding the respective exam.

The user may acknowledge receipt of a higher-priority exam or information regarding the respective exam in any of a number of different manners, which may be initiated in one example by a long selection (e.g., long press) of the information 92 indicating the exam's designation as being higher-priority. As shown in FIG. 12a, in one example, user acknowledgement may include the user tapping and holding their finger 72h for a predetermined period of time on the information indicating the exam's designation as being higher-priority. The predetermined period of time may be set in a number of different manners, but in one example, is set to be of sufficient length to reduce the likelihood of the user initiating an unintended acknowledgement (e.g., 0.6 seconds).

Figure 12C:
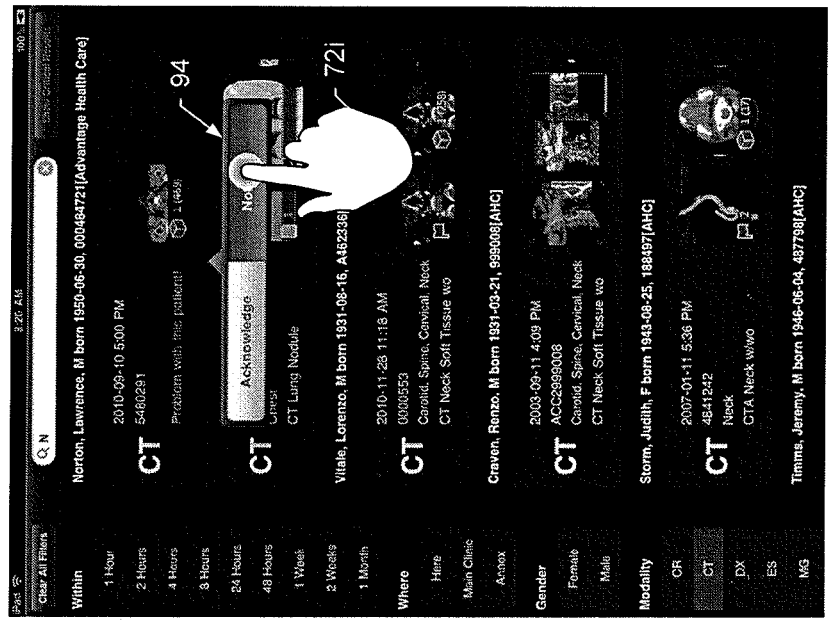
Figure 12B:
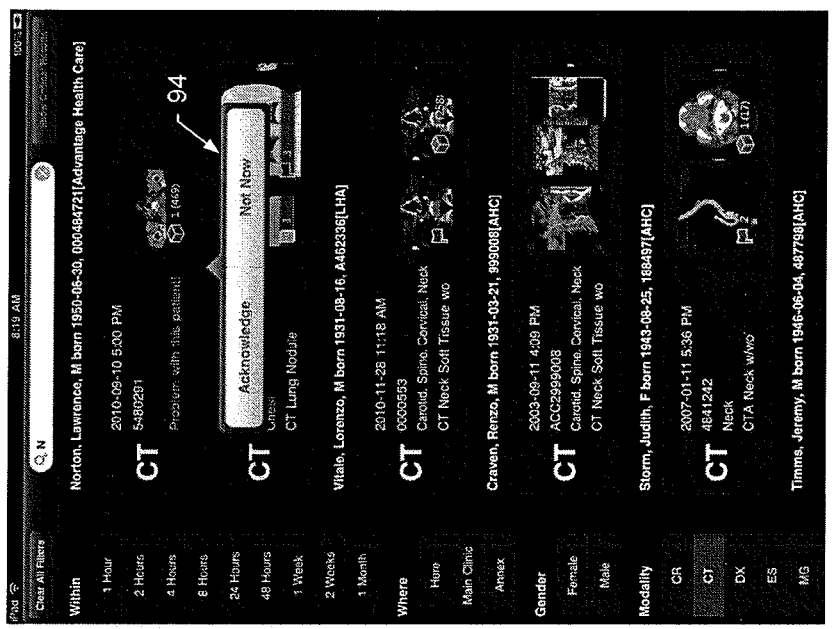

As shown in FIG. 12b, in an instance in which the user long selects—e.g., taps and holds their finger 72h for a predetermined period of time on—the appropriate information 92, the user interface may be configured to respond by presenting a dialog 94, such as a modal dialog. This dialog may include first and second selectable buttons or other selectable user interface elements by which the user may acknowledge (e.g., "Acknowledge") or defer acknowledgement of (e.g., "Not Now") receipt of the respective exam or information regarding the respective exam. As shown in FIG. 12c, the user may select to defer acknowledgement by tapping their finger 72i on a second one of the buttons; or as shown in FIG. 12d, the user may select acknowledgment by tapping their finger on a first one of the buttons. In one example, neither of the buttons of the dialog may be selected by default. Also notably, even after tapping either of the buttons the user may be required to confirm their selection. In this regard, the user interface may continue to present the dialog to thereby permit the user who has tapped one of the buttons to change their selection by tapping the other of the buttons.

Figure 12E:
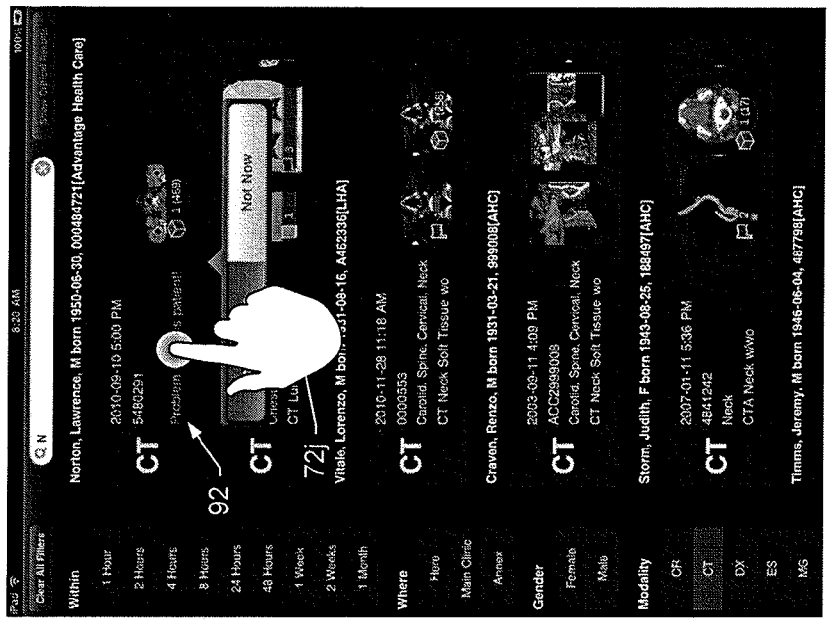
Figure 12D:
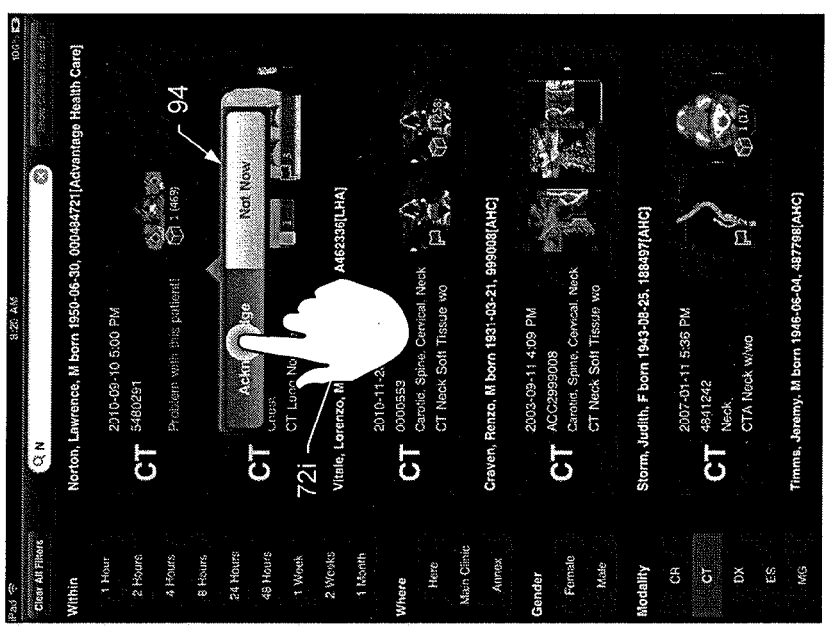
Figure 12G:
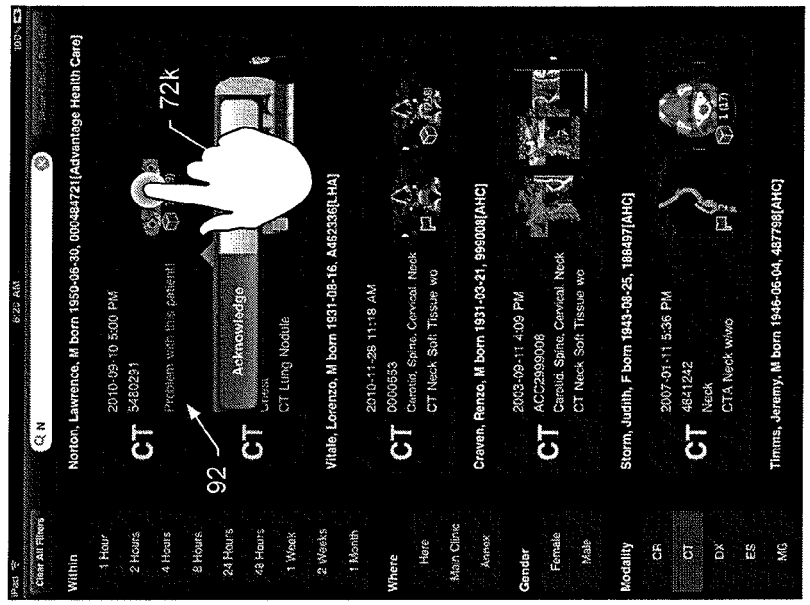
Figure 12F:
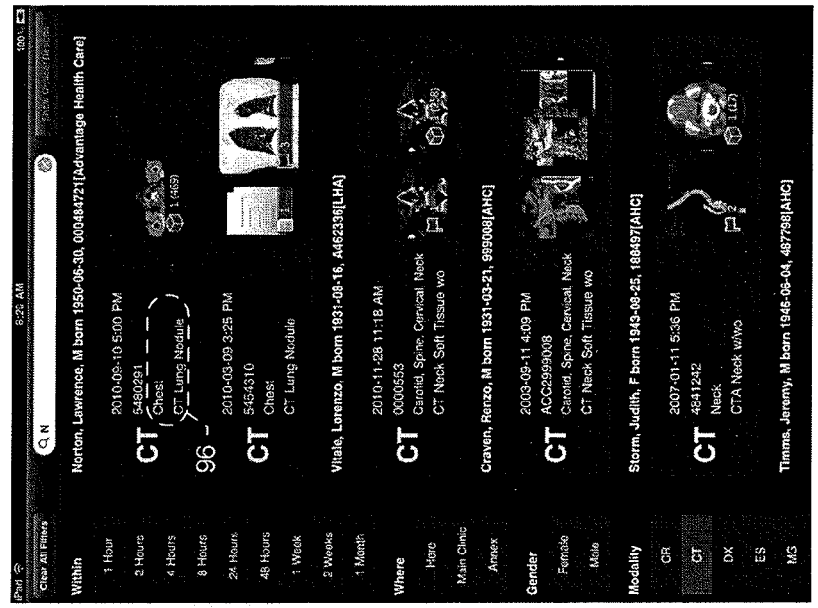

As shown in FIG. 12e, after selecting one of the buttons of the dialog 94, the user may confirm their selection by tapping their finger 72j on the information 92 indicating the exam's designation as being higher-priority, which interaction may or may not require the user to hold their finger on the information for any particular period of time. In an instance in which the user confirms their selection of acknowledgment, the user interface may respond by removing from the exam information in the list of patient exams, the information 92 indicating the exam's designation as being higher-priority. As shown in FIG. 12f, in an instance in which this information has been included in place of other information regarding the exam, the respective other information 96 may then be presented in the list of patient exams.

The dialog 94 may be dismissed without acknowledging the exam in a number of different manners. In one example, the dialog may be dismissed by the user confirming their selection in the dialog to defer acknowledgment. In another example, as shown in FIG. 12g, the dialog may be dismissed by the user tapping their finger 72k on an area of the user interface view other than on the information 92 indicating the exam's designation as being higher-priority. In this second example, the dialog may be dismissed without acknowledging the exam even in an instance in which the user has selected (but not confirmed) acknowledgment of the exam. Thus, in one example, successful acknowledgment of an exam may require the user to first tap or otherwise select the appropriate button of the dialog, and then tap the information 92 indicating the exam's designation as being higher-priority.

According to one aspect of the present invention, all or a portion of the workstation 12 and/or server 14 of exemplary embodiments of the present invention, generally operate under control of a computer program. The computer program for performing the methods of exemplary embodiments of the present invention may include one or more computer-readable program code portions, such as a series of computer instructions, embodied or otherwise stored in a computer-readable storage medium, such as the non-volatile storage medium.

FIG. 3 is a flowchart reflecting methods, systems and computer programs according to exemplary embodiments of the present invention. It will be understood that each block or step of the flowchart, and combinations of blocks in the flowchart, may be implemented by various means, such as hardware, firmware, and/or software including one or more computer program instructions. As will be appreciated, any such computer program instructions may be loaded onto a computer or other programmable apparatus to produce a machine, such that the instructions which execute on the computer or other programmable apparatus (e.g., hardware) create means for implementing the functions specified in the block(s) or step(s) of the flowchart. These computer program instructions may also be stored in a computer-readable memory that may direct a computer or other programmable apparatus to function in a particular manner, such that the instructions stored in the computer-readable memory produce an article of manufacture including instruction means which implement the function specified in the block(s) or step(s) of the flowchart. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the block(s) or step(s) of the flowchart.

Accordingly, blocks or steps of the flowchart support combinations of means for performing the specified functions, combinations of steps for performing the specified functions and program instruction means for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. It should therefore be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising a processor and a memory storing executable instructions that in response to execution by the processor cause the apparatus to at least:
   direct presentation of a user interface having a list that presents information regarding one or more elements of each of a plurality of image studies, wherein an image study comprises one or more images of a patient and information that accompanies the one or more images, wherein one or more of the plurality of image studies is designated as being of higher priority than others of the plurality of image studies as a result of the one or more higher priority image studies having information communicating an unexpected result of an examination, and for each higher-priority image study, the information presented by the list of image studies includes selectable information indicating the image study's designation as being higher priority; and
   receive an indication of user acknowledgment of receipt of a higher-priority image study or information regarding the higher-priority image study, including in order:
      receive an indication of user long selection of the information indicating the respective image study's designation as being higher priority that is presented upon the user interface, wherein the indication of the user long selection comprises an indication that the user holds their finger for at least a predetermined period of time upon the user interface to select the information;
      in response to receipt of the indication of the user long selection, direct presentation of a dialog that includes a selectable user interface element for the acknowledgment;
      receive an indication of user selection of the selectable user interface element of the dialog; and
      in response to receipt of the indication of the user selection of the selectable user interface element of the dialog, remove the higher priority designation from the respective image study such that the respective image study is no longer designated as being of higher priority following receipt of the indication of the user selection of the selectable user interface element of the dialog;
      wherein the indication of user selection of the information indicating the respective image study's designation as being higher priority is received without first receiving an indication of user interaction with any other area of the user interface.

2. The apparatus of claim 1, wherein the apparatus being caused to receive an indication consists of the apparatus being caused to receive the indication of user long selection of the information, direct presentation of the dialog that includes the selectable user interface element, receive the indication of user selection of the selectable user interface element, and receive the indication of user selection of the information.

3. The apparatus of claim 1, wherein the memory stores further executable instructions that in response to execution by the processor cause the apparatus to further:
   direct adjustment of the user interface in response to receipt of the indication of user acknowledgment of receipt of a higher-priority image study or information regarding the higher-priority image study, including direct removal from the list of image studies of the information indicating the respective image study's designation as being higher priority.

4. The apparatus of claim 1, wherein the apparatus being caused to receive an indication of user acknowledgment includes being caused to receive an indication of user acknowledgment of receipt of a first higher-priority image study or information regarding the first higher-priority image study, and wherein the memory stores further executable instructions that in response to execution by the processor cause the apparatus to further:

receive an indication of user deferral of acknowledgment of receipt of a second higher-priority image study or information regarding the second higher-priority image study, including:

receive an indication of user long selection of the information indicating the respective second image study's designation as being higher priority;

direct presentation of the dialog that includes a first selectable user interface element for the acknowledgment, and a second selectable user interface element for the deferral of the acknowledgment;

receive an indication of user selection of the second selectable user interface element; and receive an indication of user selection of the information indicating the respective image study's designation as being higher priority, without first receiving an indication of user interaction with any other area of the user interface.

5. The apparatus of claim 1, wherein the apparatus being caused to receive an indication of user acknowledgment includes being caused to receive an indication of user acknowledgment of receipt of a first higher-priority image study or information regarding the first higher-priority image study, and wherein the memory stores further executable instructions that in response to execution by the processor cause the apparatus to further:

receive an indication of user deferral of acknowledgment of receipt of a second higher-priority image study or information regarding the second higher-priority image study, including in order:

receive an indication of user long selection of the information indicating the respective second image study's designation as being higher priority;

direct presentation of the dialog that includes a first selectable user interface element for the acknowledgment, and a second selectable user interface element for the deferral of the acknowledgment;

receive an indication of user selection of either the first selectable user interface element or second selectable user interface element; and receive an indication of user interaction with any area of the user interface other than the information indicating the respective image study's designation as being higher priority, without first receiving an indication of user selection of the information indicating the respective image study's designation as being higher priority.

6. The apparatus of claim 1, wherein the apparatus being caused to receive an indication of user acknowledgment includes being caused to receive an indication of user acknowledgment of receipt of a first higher-priority image study or information regarding the first higher-priority image study, and wherein the memory stores further executable instructions that in response to execution by the processor cause the apparatus to further:

receive an indication of user deferral of acknowledgment of receipt of a second higher-priority image study or information regarding the second higher-priority image study, including in order:

receive an indication of user long selection of the information indicating the respective image study's designation as being higher priority;

direct presentation of a dialog that includes a selectable user interface element for the acknowledgment;

receive an indication of user selection of the selectable user interface element; and receive an indication of user interaction with any area of the user interface other than the information indicating the respective image study's designation as being higher priority, without first receiving an indication of user selection of the information indicating the respective image study's designation as being higher priority.

7. A method comprising:

directing presentation of a user interface having a list that presents information regarding one or more elements of each of a plurality of image studies, wherein an image study comprises one or more images of a patient and information that accompanies the one or more images, wherein one or more of the plurality of image studies is designated as being of higher priority than others of the plurality of image studies as a result of the one or more higher priority image studies having information communicating an unexpected result of an examination, and for each higher-priority image study, the information presented by the list of image studies includes selectable information indicating the image study's designation as being higher priority; and receiving an indication of user acknowledgment of receipt of a higher-priority image study or information regarding the higher-priority image study, including in order:

receiving an indication of user long selection of the information indicating the respective image study's designation as being higher priority that is presented upon the user interface, wherein the indication of the user long selection comprises an indication that the user holds their finger for at least a predetermined period of time upon the user interface to select the information;

in response to receipt of the indication of the user long selection, directing presentation of a dialog that includes a selectable user interface element for the acknowledgment;

receiving an indication of user selection of the selectable user interface element of the dialog; and in response to receipt of the indication of the user selection of the selectable user interface element of the dialog, removing the higher priority designation from the respective image study such that the respective image study is no longer designated as being of higher priority following receipt of the indication of the user selection of the selectable user interface element of the dialog;

wherein the indication of user selection of the information indicating the respective image study's designation as being higher priority is received without first receiving an indication of user interaction with any other area of the user interface, wherein directing presentation of a user interface and receiving an indication of user acknowledgment are performed by an apparatus including a processor and a memory storing executable instructions that in response to execution by the processor cause the apparatus to at least direct presentation of the user interface and receive the indication of user acknowledgment.

8. The method of claim 7, wherein receiving an indication consists of receiving the indication of user long selection of the information, directing presentation of the dialog that includes the selectable user interface element, receiving the indication of user selection of the selectable user interface element, and receiving the indication of user selection of the information.

9. The method of claim 7 further comprising:
directing adjustment of the user interface in response to receipt of the indication of user acknowledgment of receipt of a higher-priority image study or information regarding the higher-priority image study, including directing removal from the list of image studies of the information indicating the respective image study's designation as being higher priority.

10. The method of claim 7, wherein receiving an indication of user acknowledgment includes receiving an indication of user acknowledgment of receipt of a first higher-priority image study or information regarding the first higher-priority image study, and wherein the method further comprises:
receiving an indication of user deferral of acknowledgment of receipt of a second higher-priority image study or information regarding the second higher-priority image study, including:
receiving an indication of user long selection of the information indicating the respective second image study's designation as being higher priority;
directing presentation of the dialog that includes a first selectable user interface element for the acknowledgment, and a second selectable user interface element for the deferral of the acknowledgment;
receiving an indication of user selection of the second selectable user interface element; and
receiving an indication of user selection of the information indicating the respective image study's designation as being higher priority, without first receiving an indication of user interaction with any other area of the user interface.

11. The method of claim 7, wherein receiving an indication of user acknowledgment includes receiving an indication of user acknowledgment of receipt of a first higher-priority image study or information regarding the first higher-priority image study, and wherein the method further comprises:
receiving an indication of user deferral of acknowledgment of receipt of a second higher-priority image study or information regarding the second higher-priority image study, including in order:
receiving an indication of user long selection of the information indicating the respective second image study's designation as being higher priority;
directing presentation of the dialog that includes a first selectable user interface element for the acknowledgment, and a second selectable user interface element for the deferral of the acknowledgment;
receiving an indication of user selection of either the first selectable user interface element or second selectable user interface element; and
receiving an indication of user interaction with any area of the user interface other than the information indicating the respective image study's designation as being higher priority, without first receiving an indication of user selection of the information indicating the respective image study's designation as being higher priority.

12. The method of claim 7, wherein receiving an indication of user acknowledgment includes receiving an indication of user acknowledgment of receipt of a first higher-priority image study or information regarding the first higher-priority image study, and wherein the method further comprises:
receiving an indication of user deferral of acknowledgment of receipt of a second higher-priority image study or information regarding the second higher-priority image study, including in order:
receiving an indication of user long selection of the information indicating the respective image study's designation as being higher priority;
directing presentation of a dialog that includes a selectable user interface element for the acknowledgment;
receiving an indication of user selection of the selectable user interface element; and
receiving an indication of user interaction with any area of the user interface other than the information indicating the respective image study's designation as being higher priority, without first receiving an indication of user selection of the information indicating the respective image study's designation as being higher priority.

13. A computer-readable storage medium having computer-readable program code portions stored therein that in response to execution by a processor cause an apparatus to at least:
direct presentation of a user interface having a list that presents information regarding one or more elements of each of a plurality of image studies, wherein an image study comprises one or more images of a patient and information that accompanies the one or more images, wherein one or more of the plurality of image studies is designated as being of higher priority than others of the plurality of image studies as a result of the one or more higher priority image studies having information communicating an unexpected result of an examination, and for each higher-priority image study, the information presented by the list of image studies includes selectable information indicating the image study's designation as being higher priority; and
receive an indication of user acknowledgment of receipt of a higher-priority image study or information regarding the higher-priority image study, including in order:
receive an indication of user long selection of the information indicating the respective image study's designation as being higher priority that is presented upon the user interface, wherein the indication of the user long selection comprises an indication that the user holds their finger for at least a predetermined period of time upon the user interface to select the information;
in response to receipt of the indication of the user long selection, direct presentation of a dialog that includes a selectable user interface element for the acknowledgment; and
receive an indication of user selection of the selectable user interface element of the dialog; and
in response to receipt of the indication of the user selection of the selectable user interface element of the dialog, remove the higher priority designation from the respective image study such that the respective image study is no longer designated as being of higher priority following receipt of the indication of the user selection of the selectable user interface element of the dialog;
wherein the indication of user selection of the information indicating the respective image study's designation as being higher priority is received without first receiving an indication of user interaction with any other area of the user interface.

14. The computer-readable storage medium of claim 13, wherein the apparatus being caused to receive an indication consists of the apparatus being caused to receive the indication of user long selection of the information, direct presentation of the dialog that includes the selectable user interface element, receive the indication of user selection of the selectable user interface element, and receive the indication of user selection of the information.

15. The computer-readable storage medium of claim 13, wherein the computer-readable storage medium has further computer-readable program code portions stored therein that in response to execution by the processor cause the apparatus to further:

direct adjustment of the user interface in response to receipt of the indication of user acknowledgment of receipt of a higher-priority image study or information regarding the higher-priority image study, including direct removal from the list of image studies of the information indicating the respective image study's designation as being higher priority.

16. The computer-readable storage medium of claim 13, wherein the apparatus being caused to receive an indication of user acknowledgment includes being caused to receive an indication of user acknowledgment of receipt of a first higher-priority image study or information regarding the first higher-priority image study, and wherein the computer-readable storage medium has further computer-readable program code portions stored therein that in response to execution by the processor cause the apparatus to further:

receive an indication of user deferral of acknowledgment of receipt of a second higher-priority image study or information regarding the second higher-priority image study, including:

receive an indication of user long selection of the information indicating the respective second image study's designation as being higher priority;

direct presentation of the dialog that includes a first selectable user interface element for the acknowledgment, and a second selectable user interface element for the deferral of the acknowledgment;

receive an indication of user selection of the second selectable user interface element; and receive an indication of user selection of the information indicating the respective image study's designation as being higher priority, without first receiving an indication of user interaction with any other area of the user interface.

17. The computer-readable storage medium of claim 13, wherein the apparatus being caused to receive an indication of user acknowledgment includes being caused to receive an indication of user acknowledgment of receipt of a first higher-priority image study or information regarding the first higher-priority image study, and wherein the computer-readable storage medium has further computer-readable program code portions stored therein that in response to execution by the processor cause the apparatus to further:

receive an indication of user deferral of acknowledgment of receipt of a second higher-priority image study or information regarding the second higher-priority image study, including in order:

receive an indication of user long selection of the information indicating the respective second image study's designation as being higher priority;

direct presentation of the dialog that includes a first selectable user interface element for the acknowledgment, and a second selectable user interface element for the deferral of the acknowledgment;

receive an indication of user selection of either the first selectable user interface element or second selectable user interface element; and receive an indication of user interaction with any area of the user interface other than the information indicating the respective image study's designation as being higher priority, without first receiving an indication of user selection of the information indicating the respective image study's designation as being higher priority.

18. The computer-readable storage medium of claim 13, wherein the apparatus being caused to receive an indication of user acknowledgment includes being caused to receive an indication of user acknowledgment of receipt of a first higher-priority image study or information regarding the first higher-priority image study, and wherein the computer-readable storage medium has further computer-readable program code portions stored therein that in response to execution by the processor cause the apparatus to further:

receive an indication of user deferral of acknowledgment of receipt of a second higher-priority image study or information regarding the second higher-priority image study, including in order:

receive an indication of user long selection of the information indicating the respective image study's designation as being higher priority;

direct presentation of a dialog that includes a selectable user interface element for the acknowledgment;

receive an indication of user selection of the selectable user interface element; and receive an indication of user interaction with any area of the user interface other than the information indicating the respective image study's designation as being higher priority, without first receiving an indication of user selection of the information indicating the respective image study's designation as being higher priority.

* * * * *